(12) United States Patent
Stieber et al.

(10) Patent No.: US 10,265,116 B2
(45) Date of Patent: Apr. 23, 2019

(54) DEVICE FOR THE PLANAR TREATMENT OF AREAS OF HUMAN OR ANIMAL SKIN OR MUCOUS MEMBRANE SURFACES BY MEANS OF A COLD ATMOSPHERIC PRESSURE PLASMA

(71) Applicants: Manfred Stieber, Greifswald (DE); Klaus-Dieter Weltmann, Binz (DE); Stefan Horn, Greifswald (DE); Ronny Brandenburg, Gross Kiesow (DE); Thomas Von Woedtke, Horst (DE)

(72) Inventors: Manfred Stieber, Greifswald (DE); Klaus-Dieter Weltmann, Binz (DE); Stefan Horn, Greifswald (DE); Ronny Brandenburg, Gross Kiesow (DE); Thomas Von Woedtke, Horst (DE)

(73) Assignee: LEIBNIZ-INSTITUT FUER PLASMAFORSCHUNG UND TECHNOLOGIE E.V, Greifswald (DE)

( * ) Notice: Subject to any disclaimer, the term of this patent is extended or adjusted under 35 U.S.C. 154(b) by 529 days.

(21) Appl. No.: 14/732,387

(22) Filed: Jun. 5, 2015

(65) Prior Publication Data
US 2016/0045246 A1 Feb. 18, 2016

Related U.S. Application Data

(63) Continuation of application No. 13/392,221, filed as application No. PCT/EP2010/060859 on Jul. 27, 2010, now abandoned.

(30) Foreign Application Priority Data
Aug. 25, 2009 (DE) .................... 20 2009 011 521 U

(51) Int. Cl.
*A61B 18/04* (2006.01)
*A61N 1/18* (2006.01)
(Continued)

(52) U.S. Cl.
CPC .............. *A61B 18/042* (2013.01); *A61N 1/18* (2013.01); *A61N 1/44* (2013.01); *H05H 1/2406* (2013.01);
(Continued)

(58) Field of Classification Search
CPC ................................ A61B 18/042; A61N 1/18
See application file for complete search history.

(56) References Cited

U.S. PATENT DOCUMENTS

| 4,940,894 A | 7/1990 | Morters |
| 7,008,596 B1 | 3/2006 | Rump et al. |

(Continued)

FOREIGN PATENT DOCUMENTS

| DE | 101 27 035 | 2/2002 |
| DE | 10127035 | 2/2002 |

(Continued)

OTHER PUBLICATIONS

International Search Report dated Dec. 16, 2010 in PCT/Ep10/60859 Filed Jul. 27, 2010.

*Primary Examiner* — Bhisma Mahta
*Assistant Examiner* — Matthew A Engel
(74) *Attorney, Agent, or Firm* — Soroker Agmon Nordman

(57) ABSTRACT

The invention relates to a device, preferably a collar, for treating areas of human or animal skin or mucous membrane with a cold atmospheric pressure plasma by creating a dielectrically hindered surface discharge, comprising at least one flexible insulating material (1), a flexible high-voltage electrode (2), a flexible dielectric (3), a flexible grounded (Continued)

Figure 1:
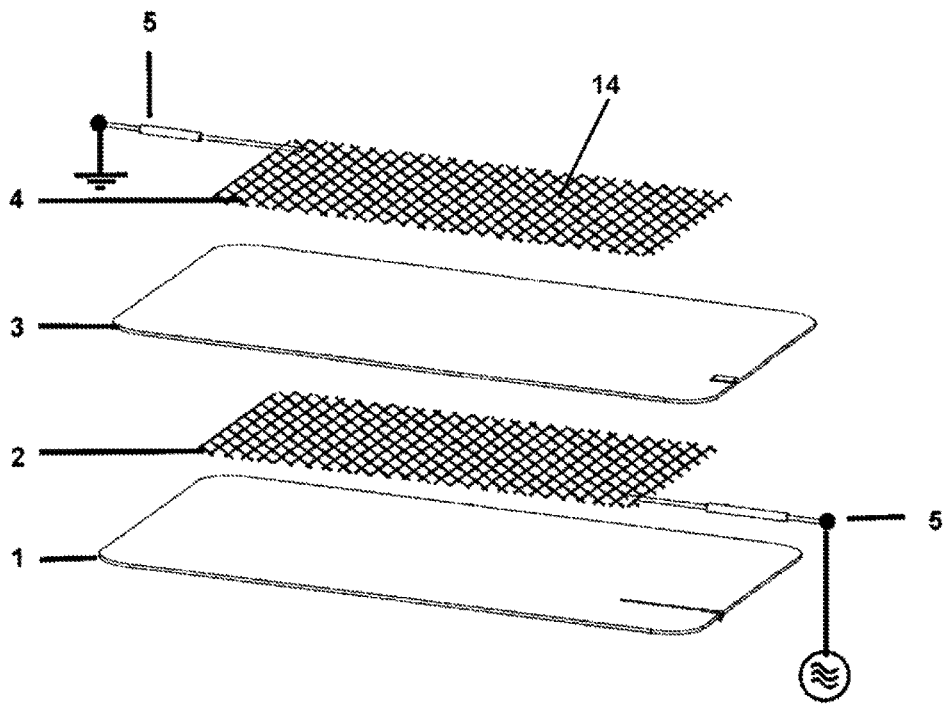

electrode (4) and a gas supply (7), characterized in that the flexible high-voltage electrode (2) is embedded in the insulating elastomer (3), having the effect of a dielectric, and the grounded electrode (4) is applied to the elastomer surface facing the surface to be treated.

9 Claims, 5 Drawing Sheets

(51) Int. Cl.
    *A61N 1/44*     (2006.01)
    *H05H 1/24*     (2006.01)
    *A61B 18/00*     (2006.01)

(52) U.S. Cl.
    CPC ............ *A61B 2018/00452* (2013.01); *A61B 2018/00583* (2013.01); *H05H 2240/20* (2013.01); *H05H 2245/122* (2013.01)

(56) References Cited

U.S. PATENT DOCUMENTS

| | | | |
|---|---|---|---|
| 7,540,283 B2 | 6/2009 | Loori et al. | |
| 7,655,005 B2 | 2/2010 | Bhola | |
| 2006/0196424 A1 | 9/2006 | Swallow | |
| 2007/0014752 A1 | 1/2007 | Roy | |
| 2010/0292757 A1* | 11/2010 | Ehlbeck ................. | B29C 59/14 607/50 |
| 2011/0112528 A1* | 5/2011 | Stieber .................. | A61L 2/0011 606/41 |
| 2012/0271225 A1* | 10/2012 | Stieber ................. | A61B 18/042 604/26 |
| 2013/0053760 A1* | 2/2013 | Ehlbeck .................. | H05H 1/24 604/23 |
| 2014/0207208 A1 | 7/2014 | Chapman-Jones | |
| 2015/0088234 A1* | 3/2015 | Weltmann ............ | A61B 18/042 607/104 |
| 2016/0008500 A1* | 1/2016 | Ehlbeck .................... | A61L 2/14 427/230 |
| 2017/0136252 A1* | 5/2017 | Weltmann ................ | A61N 1/44 |
| 2017/0231680 A1* | 8/2017 | Mahrenholz ......... | A61B 18/042 606/34 |

FOREIGN PATENT DOCUMENTS

| | | |
|---|---|---|
| DE | 10 2007 030 915 | 1/2009 |
| DE | 102007030915 | 1/2009 |
| EP | 1 023 003 | 5/2008 |
| JP | 2008 34184 | 2/2008 |
| JP | 2008034184 | 2/2008 |
| WO | 2004 068916 | 8/2004 |
| WO | 2006/001455 | 1/2006 |
| WO | 2006 001455 | 1/2006 |
| WO | WO 2006/116252 | 11/2006 |
| WO | 2006/116252 | 8/2007 |
| WO | 2009 019156 | 2/2009 |
| WO | 2009 06782 | 5/2009 |
| WO | 2009/067682 | 5/2009 |
| WO | 2009/067682 | 8/2009 |

* cited by examiner

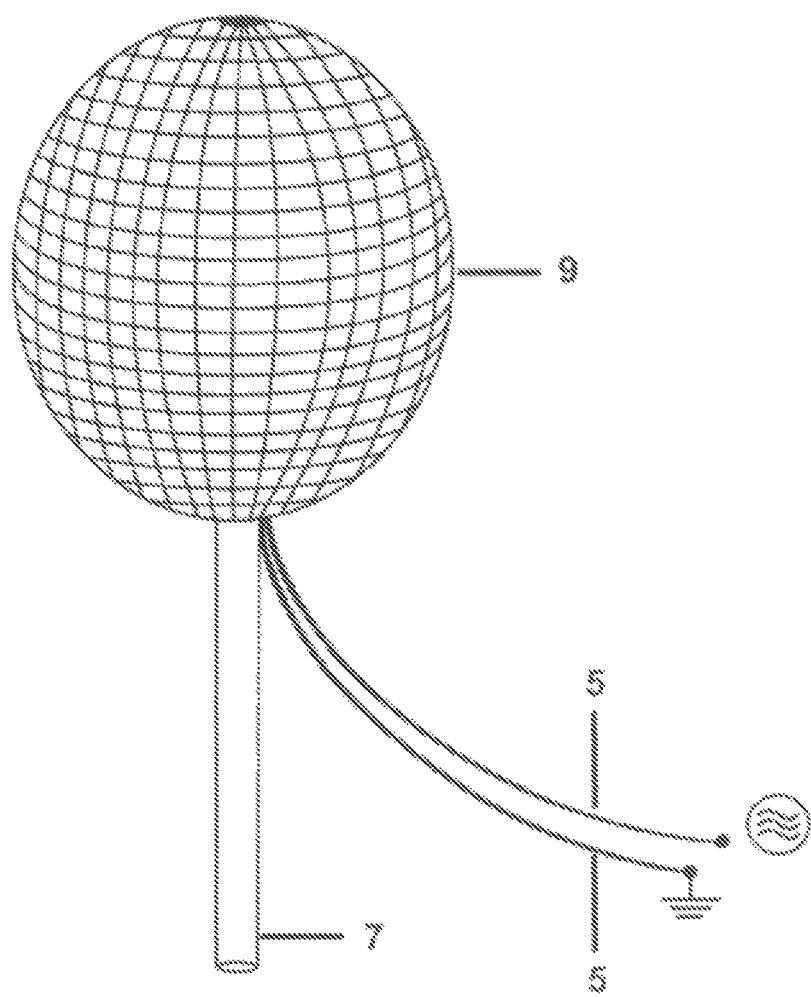

DEVICE FOR THE PLANAR TREATMENT OF AREAS OF HUMAN OR ANIMAL SKIN OR MUCOUS MEMBRANE SURFACES BY MEANS OF A COLD ATMOSPHERIC PRESSURE PLASMA

The invention relates to a device for surface treatment of areas of human or animal skin or mucous membrane surfaces by means of a cold atmospheric-pressure plasma. The centerpiece of the device is a special electrode arrangement for generating a dielectric barrier surface discharge, which can be applied flexibly onto arbitrarily curved surfaces. On the basis of this invention, it is possible to generate, in the region of diseased skin or mucous membrane parts of the human body, in the immediate proximity of the skin or mucous membrane surface or of wounds, a superficial plasma for treatment of diseased areas, which plasma is safe as regards the stress on the skin or mucous membrane due to temperature and electrical voltages.

PRIOR ART

As the result of scientific studies of recent years, new application possibilities are now being opened up in some areas of biology and medicine for plasma technology, which has already proved to be a key technology for diverse applications of surface treatments in industry ([1] M. Laroussi, "Low-Temperature Plasmas for Medicine?", IEEE Transactions on Plasma Science 2009, 37, 714-725; [2] M. Kong et al., Plasma medicine: "an introductory review", New Journal of Physics 2009, 11, 115012; [3] G. Lloyd et at, "Gas Plasma: Medical Uses and Developments in Wound Care", Plasma Processes and Polymers 2010, 7, 194-211).

The potential of plasma technology for applications of this type is rated as sufficiently important that an independent discipline known as plasma medicine is now beginning to develop on the international front. One of its substantial objectives, for example, is the development of innovative therapeutic methods for treating skin or mucous membrane diseases and chronic wounds with cold atmospheric-pressure plasmas, on the basis of the interaction of antiseptic plasma effect and stimulation of new growth of healthy tissue by the plasma.

In order that plasma-based therapeutic approaches of this type can be systematically developed and employed, suitable plasma sources are needed that on the one hand work painlessly and ensure that the tissue to be treated is not harmed by temperature, desiccation or electrical voltages, and on the other hand can be used flexibly for large-area applications for various body regions under variable plasma conditions.

Devices for plasma treatment of living tissue with non-thermal atmospheric plasmas have been proposed in several publications (DE 3618412 A1, WO 2004/105810 A1, WO 2006/116252 A2). The devices described in these publications are equipped with rigid electrode systems or nozzles for generation of atmospheric-pressure plasmas in the region of the tissue surfaces to be treated, and so they permit only local treatment of relatively small areas.

OBJECT OF THE INVENTION

The object of the invention was to find a technical solution for generation of a superficial plasma that makes it possible to treat relatively large areas of body parts, especially of arbitrarily curved areas of human or animal skin or mucous membrane.

OUTLINE OF THE INVENTION

The object is achieved according to the features of the claims. According to the invention, an electrode system for generating a dielectric barrier surface discharge is provided that on the one hand is composed of flexible materials, so that it can be conformed to curved surfaces, and on the other hand has an outer, electrically conductive surface, which is used as a grounded electrode and is structured in such a way that dielectric barrier surface discharges can form in the interstices of the structure that remain open.

A substantial advantage of the invention that is important especially for wound healing is the fact among others that, because of the design as a cuff that conforms to the body, the treated area is covered and thus is protected from desiccation, whereby the moist environment necessary according to the prior art for wound healing is better assured than during the application of open, rigid electrode systems with a gas flow that may be necessary. The design as a DBD (dielectric barrier discharge) without or with a small gas flow also counteracts the danger of desiccation.

A further advantage of the invention is that the elastic electrode system can also be configured as a shapeable (inflatable) volume (for example, as a silicone ball), in such a way that treatments on the one hand of the mucous membrane surfaces of body cavities and on the other hand of arbitrarily shaped skin or mucous membrane areas can be performed with the plasma generated on the inner or outer surface of this electrode system.

This arrangement offers the possibility of a combination with catheters, endoscopes and surgical instruments. It works both at atmospheric pressure and at slight overpressure or underpressure, with use of different gases or gas mixtures, if appropriate in combination with the transport of active substances, and is usable for diverse applications toward decontamination, sterilization, antisepsis, wound healing, etc., both in medicine and in other areas of the life sciences. Slight overpressure or underpressure means that only minor deviations from atmospheric pressure are involved here.

Subject matter of the invention is also a method for treating areas of human or animal skin or mucous membrane surfaces by means of a cold atmospheric-pressure plasma. The inventive method consists in the fact that an electrode system of flexible materials for generating a dielectric barrier surface discharge is provided, so that it can be conformed to curved surfaces, and that the electrode system has an outer, electrically conductive surface, which is used and structured as a grounded electrode, wherein a dielectric barrier surface discharge is generated in the interstices of the structure that remain open.

In a preferred embodiment of the method, it is possible to shape the elastic materials for electrodes and dielectric into a surface with a closed volume, preferably a silicone balloon, and to ignite a plasma both on the inside of the hollow body and on the outside.

EXAMPLES

The invention will be explained in more detail on the basis of figures, without being restricted to these figures.

Figure 2:
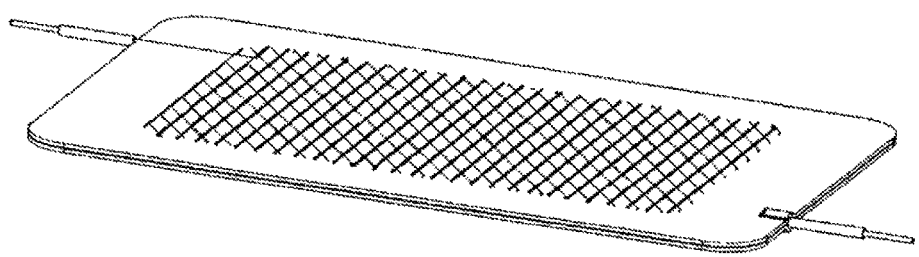
Figure 3:
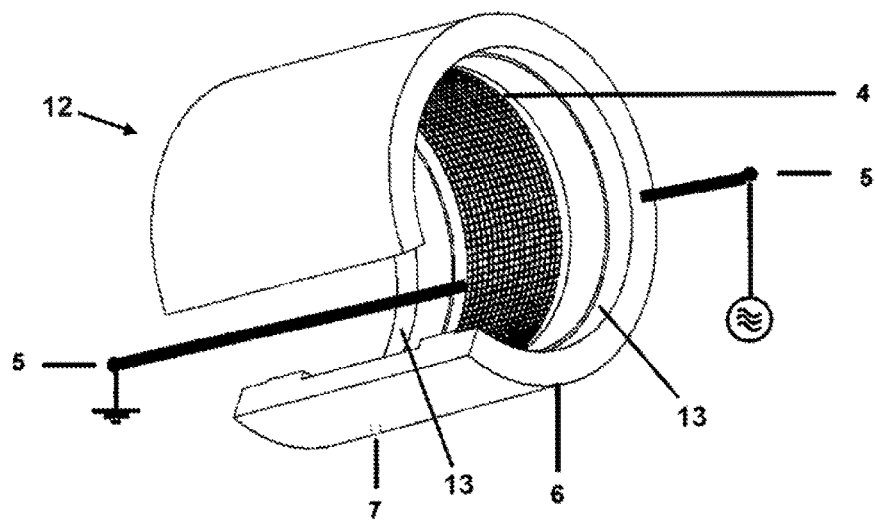
Figure 4:
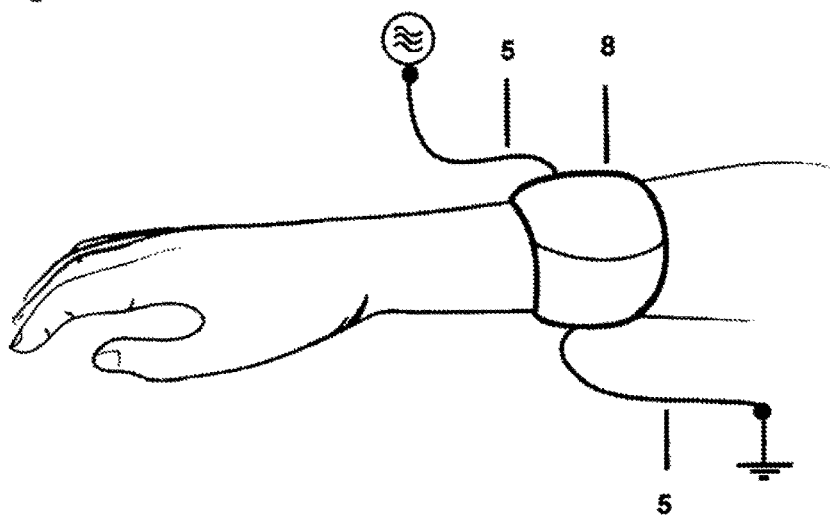
Figure 6A:
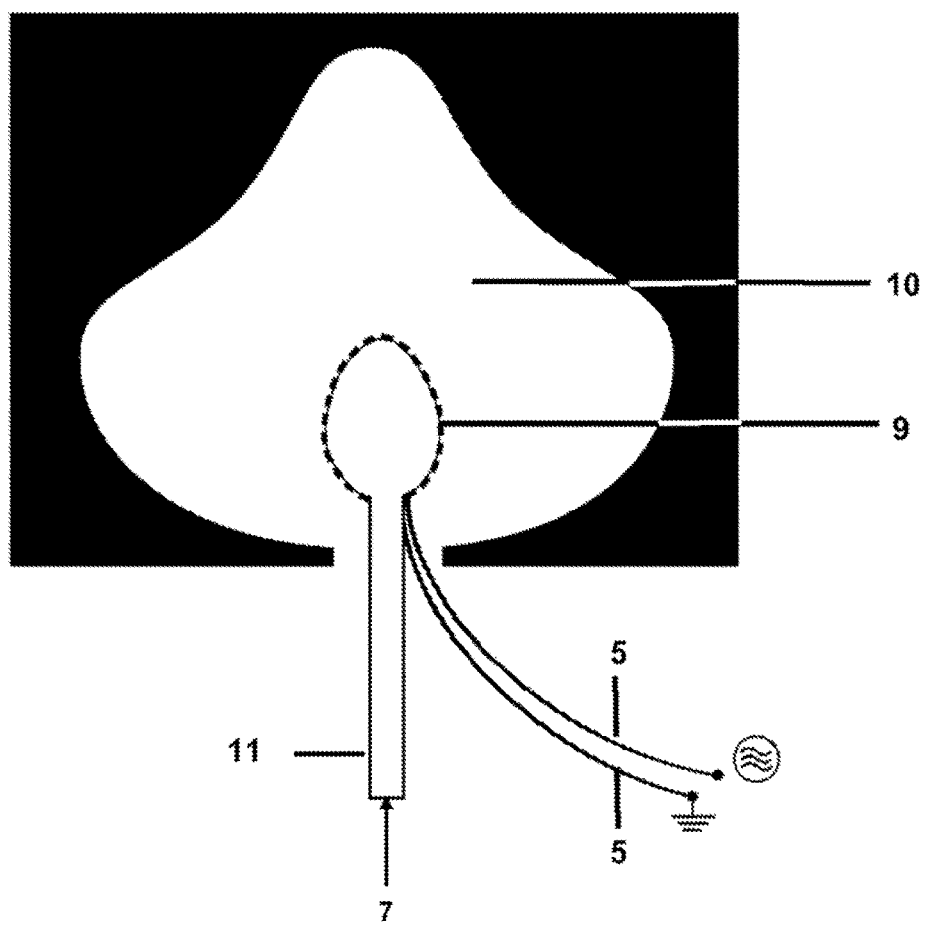
Figure 6B:
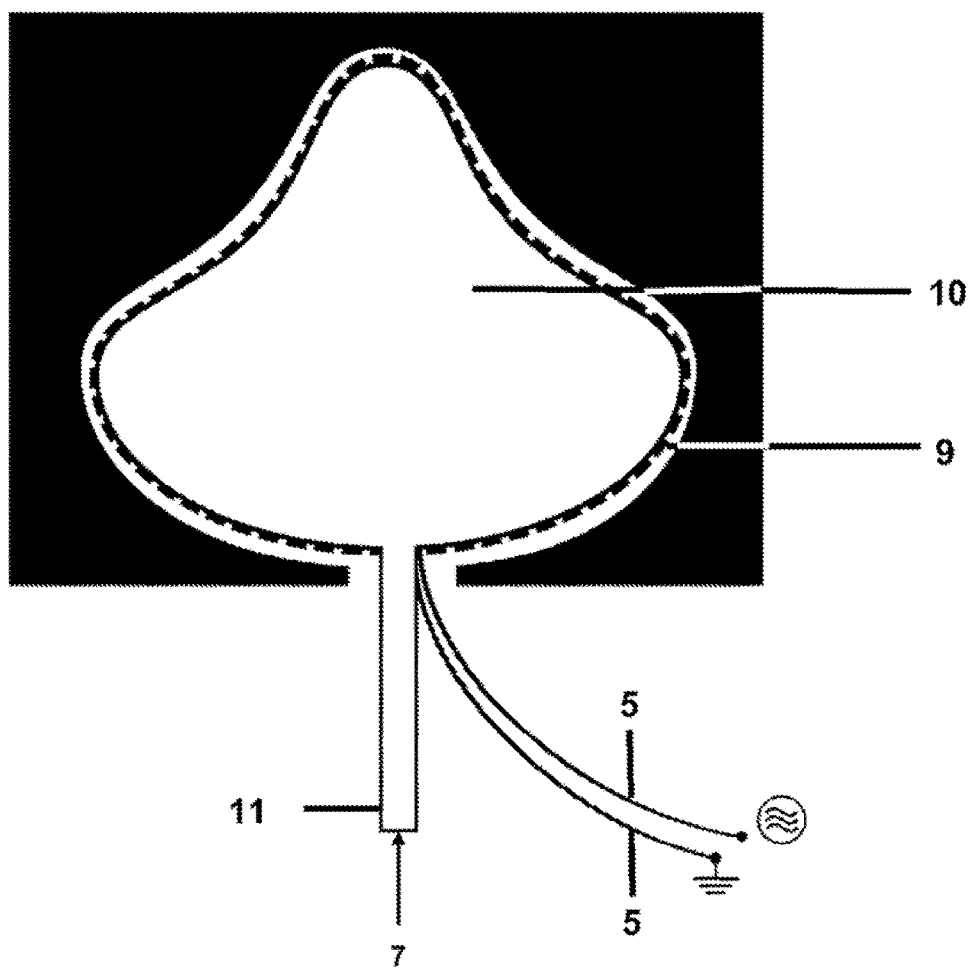

For this purpose FIGS. 1 and 2 show the basic structure of the inventive device. Of those, FIG. 2 is the assembled planar electrode arrangement while FIG. 1 represents an exploded view of this arrangement for demonstration purposes. FIG. 3 shows an exemplary embodiment in curved form with a gas port for the optional supply of a process gas, and FIG. 4 shows an exemplary embodiment of an arm cuff. The basic structure of an electrode system configured as a shapeable silicone ball is schematically illustrated in FIG. 5, and the application of such an inflatable plasma source for treating the inner surface of body cavities in combination with an endoscope is schematically illustrated in FIGS. 6*a* and 6*b*.

REFERENCE NUMERAL LIST

The following reference numerals are used for the attached drawings:
1 Flexible insulating material (such as elastomer, silicone film)
2 Flexible high-voltage electrode (such as metal gauze, metal foil, electrically conductive elastomer)
3 Flexible dielectric (such as elastomer, silicone film)
4 Grounded electrode: flexible and structured (such as metal gauze, structured metal foil, structured electrically conductive elastomer)
5 Electrical connecting cable
6 Insulating elastomer with embedded flexible high-voltage electrode
7 Gas supply
8 Arm cuff
9 Balloon of elastic materials (dielectric with embedded electrodes)
10 Body cavity
11 Endoscope coupling
12 Medical strip
13 Adhesive points
14 Interstices of the structure that remain open

The invention claimed is:

1. A device for treatment of areas of human or animal skin, mucous membrane, or body parts with a cold atmospheric-pressure plasma by generating a dielectric barrier surface discharge, comprising:
at least one flexible insulating material (1),
a planar flexible high-voltage electrode (2),
a planar flexible dielectric (3),
a planar flexible grounded electrode (4),
a gas supply (7),
wherein the flexible high-voltage electrode (2) is embedded between the at least one flexible insulating material (1) and the flexible dielectric (3), and wherein the grounded electrode (4) is applied on a surface of the flexible dielectric (3) that faces a curved surface of a body part to be treated, wherein the flexible high-voltage electrode (2), the flexible dielectric (3) and the flexible grounded electrode (4) of the device form a flexible layered arrangement for providing the cold atmospheric pressure plasma, wherein said flexible layered arrangement is conformed to be wrapped flexibly around the curved surface of the body part for treating said curved surface with the cold atmospheric pressure plasma generated by the device.

2. The device according to claim 1, wherein the device is a flexible cuff (8) or a medical strip (12).

3. The flexible cuff (8) according to claim 2, wherein the cuff (8) represents an arm or leg cuff.

4. The medical strip (12) according to claim 2, wherein the medical strip (12) has adhesive points (13).

5. The device according to claim 1, wherein the device comprises a power-supply unit that is operatable in pulsed mode of operation and thus offers the possibility of being able to regulate the intensity of the cold atmospheric pressure plasma within wide limits.

6. The device according to claim 1, wherein the grounded electrode (4) is structured as a grid structure, so that dielectric barrier surface discharges can form in interstices (14) of the grid structure that remain open.

7. The device according to claim 1, wherein metal gauze, metal foil or thin films of metal or conductive elastomer are used as the flexible high-voltage electrode (2) and/or the grounded electrode (4).

8. The device according to claim 1, wherein the flexible high-voltage electrode (2), the flexible dielectric (3) and the flexible grounded electrode (4) of the device are fixed to each other so as to permanently form the flexible layered arrangement for a controlled plasma generation.

9. The device according to claim 1, wherein the flexible layered arrangement is conformed to be wrapped flexibly around the curved surface of the body part, the body part being a limb, a hand, a finger, or another appendage of the human or animal.

* * * * *